US007223573B2

(12) United States Patent
Patel et al.

(10) Patent No.: US 7,223,573 B2
(45) Date of Patent: May 29, 2007

(54) ENZYMATIC AMMONOLYSIS PROCESS FOR THE PREPARATION OF INTERMEDIATES FOR DPP IV INHIBITORS

(75) Inventors: Ramesh N. Patel, Bridgewater, NJ (US); Ronald L. Hanson, Morris Plains, NJ (US); Iqbal Gill, Denville, NJ (US); David B. Brzozowski, Pattersonville, NY (US); Paul M. Skonezny, Baldwinsville, NY (US); Michael M. Politino, Syracuse, NY (US); Jason G. Chen, Manlius, NY (US); Francisco Moris-Varas, DeWitt, NY (US); Brenda J. White, Jamesville, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 114 days.

(21) Appl. No.: 11/119,552

(22) Filed: May 2, 2005

(65) Prior Publication Data

US 2005/0256019 A1    Nov. 17, 2005

Related U.S. Application Data

(60) Provisional application No. 60/568,097, filed on May 4, 2004.

(51) Int. Cl.
*C12P 17/10*    (2006.01)
*C07D 207/22*    (2006.01)
(52) U.S. Cl. ........................ 435/121; 548/536
(58) Field of Classification Search .............. 548/531, 548/536; 435/121
See application file for complete search history.

(56) References Cited

U.S. PATENT DOCUMENTS

| 6,068,991 | A | 5/2000 | Liu et al. |
| 6,395,767 | B2 | 5/2002 | Robl et al. |
| 2005/0090539 | A1 | 4/2005 | Vu et al. |

FOREIGN PATENT DOCUMENTS

EP    0 808 824    11/1997
WO    WO 00/04179    1/2000

OTHER PUBLICATIONS

Conde et al, Journal of Molecular Catalysis B: Enzymatic, Dec. 20, 1999, 7, 299-306.*
Reetz, M.T. et al., "General Synthesis of Potentially Antiviral α-Adamantyl Carbonyl Compounds", Angew. Chem. Int. Ed. Engl., vol. 18, No. 1, p. 72 (1979).
Reetz, M.T. et al., "Lewis-Säure-bedingte α-*tert*-Alkylierung von Carbonsäuren und Carbonsäureestern", Chem. Ber., vol. 116, pp. 3708-3724 (1983).
Reetz, M.T. et al., "Regioselektive Lewis-Säure-bedingte α-*tert*-Alkylierung von Acyloinen und Glycolsäure", Chem. Ber., vol. 116, pp. 3702-3707 (1983).
Sagnard, I. et al., "Enantioselective Synthesis of Cyclopropane α-Amino Acids: Synthesis of N-Boc-*cis*-(2S,3R,4S)-3,4-Methanoproline and N-Boc-(2S,3R,4S)-3,4-Methanoglutamic Acid", Tetrahedron Letters, vol. 36, No. 18, pp. 3148-3152 (1995).
Takada, H. et al., "Thermostable Phenylalanine Dehydrogenase of *Thermoactinomyces intermedius*: Cloning, Expression, and Sequencing of Its Gene", J. Biochem., vol. 109, pp. 371-376 (1991).
Tverezovsky, V.V. et al., "Synthesis of (2S, 3R, 4S)-3,4-Methanoproline and Analogues by Cyclopropylidene Insertion", Tetrahedron, vol. 53, No. 43, pp. 14773-14792 (1997).
U.S. Appl. No. 11/091,183, filed Mar. 28, 2005, Sharma et al.
U.S. Appl. No. 11/104,015, filed Apr. 12, 2005, Politino et al.
U.S. Appl. No. 11/135,217, filed May 23, 2005, Sharma.
Hanessian, S. et al., "Probing the Importance of Spacial and Conformational Domains in Captopril Analogs for Angiotensin Converting Enzyme Activity", Bioorganic & Medicinal Chemistry Letters, vol. 8, pp. 2123-2128 (1998).
Hanson, R.L. et al., Synthesis of allysine ethylene acetal using phenylalanine dehydrogenase from *Thermoactinomyces intermedius*, Enzyme and Microbial Technology, vol. 26, pp. 348-358 (2000).
Imashiro, R. et al., "Asymmetric synthesis of methyl (2R,3S)-3-(4-methoxyphenyl) glycidate, a key intermediate of diltiazem, via Mukaiyama aldol reaction", Tetrahedron Letters, vol. 42, pp. 1313-1315 (2001).

* cited by examiner

*Primary Examiner*—Joseph K. McKane
*Assistant Examiner*—Karen Cheng
(74) *Attorney, Agent, or Firm*—Burton Rodney

(57) ABSTRACT

An enzymatic ammonolysis process is provided for the preparation of intermediates used in preparing dipeptidyl peptidase IV inhibitors wherein the enzyme *Candida antarctica* lipase-B is used to catalyze the ammonolysis process.

14 Claims, No Drawings

ENZYMATIC AMMONOLYSIS PROCESS FOR THE PREPARATION OF INTERMEDIATES FOR DPP IV INHIBITORS

FIELD OF THE INVENTION

This application claims a benefit of priority from U.S. Provisional Application No. 60/568,097, filed May 4, 2004, the entire disclosure of which is herein incorporated by reference.

The present invention relates to an enzymatic ammonolysis process for the preparation of intermediates useful in preparing dipeptidyl peptidase (DPP) IV inhibitors and to a method for preparing DPP IV inhibitors employing such intermediates.

BACKGROUND OF THE INVENTION

U.S. Provisional Application No. 60/431,814 filed Dec. 9, 2002 discloses a method for preparing the intermediate (5S)-5-aminocarbonyl-4,5-dihydro-1H-pyrrole-1-carboxylic acid, 1-(1,1-dimethylethyl)ester (Formula A)

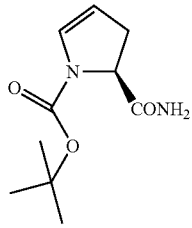

from 4,5-dihydro-1H-pyrrole-1,5-dicarboxylic acid, 1-(1,1-dimethylethyl)-5-ethyl or methyl ester (Formula B)

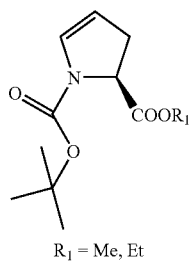

$R_1$ = Me, Et by hydrolyzing B by saponification with lithium hydroxide, and treating with mesyl chloride and ammonia to produce the Formula A intermediate.

The Formula A intermediate is useful in preparing the dipeptidyl peptidase IV inhibitor (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile

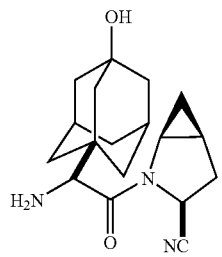

(disclosed in U.S. Pat. No. 6,395,767 which is incorporated herein by reference) as discussed in U.S. Provisional Application No. 60/431,814 which is useful in treating diabetes.

BRIEF DESCRIPTION OF THE INVENTION

In accordance with the present invention, a method is provided for the preparation of an intermediate of the structure A

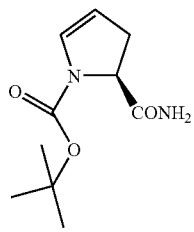

(5S)-5-aminocarbonyl-4,5-dihydro-1H-pyrrole-1-carboxylic acid, 1-(1,1-dimethylethyl)ester also referred to as (2S)-2-aminocarbonyl-2,3-dihydro-1H-pyrrole-1-carboxylic acid, 1-(1,1-dimethylethyl) ester which is useful in preparing the dipeptidyl peptidase IV inhibitor (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile disclosed in U.S. Pat. No. 6,395,767.

The method of the invention for making intermediate A includes the step of providing the compound (5S)-4,5-dihydro-1H-pyrrole-1,5-dicarboxylic acid, 1-(1,1-dimethylethyl) 5-ethyl or methyl ester having the structure B $R_1$ = Me, Et (also referred to as (2S)-1H-pyrrole-1,2-dicarboxylic acid, 2,3-dihydro-, 1-(1,1-dimethylethyl) 2-ethyl or methyl ester, respectively), and subjecting compound B to enzymatic ammonolysis in the presence of an ammonia source, such as ammonia gas, ammonium carbamate, ammonium formate, ammonium phosphate, ammonium acetate and the like to produce the intermediate A employing an enzyme, a microorganism producing the enzyme or an enzyme having the structure of an enzyme derived from the microorganism, which is capable of catalyzing ammonolysis of the compound of formula B or a salt thereof, to yield a compound of formula A or a salt thereof.

In carrying out the enzymatic ammonolysis of compound B to form A, the compound B or a toluene solution of compound B is preferably treated with (1) the enzyme *Candida antarctica* lipase-B (Cal-B), which is capable of catalyzing the ammonolysis of the compound of formula B or salt thereof, to yield the compound of formula A or salt thereof, and (2) ammonia gas and/or a source of ammonia such as ammonium carbamate, preferably in the presence of a solvent like toluene or a branched tertiary alcohol such as t-butanol, tert-amyl alcohol, or 3-methyl-3-pentanol, or methyl t-butyl ether, or a mixture of methyl t-butyl ether:t-butanol (about 4:1), at a temperature within the range from about 25° C. to about 80° C., preferably from about 40° C. to about 70° C. Molecular sieves 3A, 4A or 13X may be employed to assist in ethanol removal.

The enzyme employed in the method of the invention is a hydrolase which preferably is derived from the yeast *Candida antarctica*, and more preferably is fraction B lipase from the yeast *Candida antarctica*.

*Candida antarctica* lipase-B is commercially available in both soluble, powder and immobilized formulations and in lyophilized formulations.

The enzymatic ammonolysis reaction of the compound B to form compound A produces ethanol and when using ammonium carbamate, carbon dioxide. Various additives may be included in the reaction to push the reaction to the amide compound A. Thus, to assist ethanol removal, $CaCl_2$, soda lime, CaO, $Ca(OH)_2$, $Mg(OH)_2$ or $Na_2CO_3$ (preferably $CaCl_2$) may be added. The ethanol removal additive may be employed in an amount within the range from about 1 to about 10 mole equivalent per mole of ester compound B, preferably from about 1 to about 4 mole equivalent per mole of ester compound B. Alternatively, molecular sieves 3A, 4A or 13X may be employed to assist in ethanol removal.

To assist in $CO_2$ removal, an alkali metal oxide, hydroxide or carbonate such as NaOH, KOH, $Na_2CO_3$ or soda lime, preferably NaOH, or an alkaline earth metal oxide, hydroxide or carbonate such as CaO, $Ca(OH)_2$, $Mg(OH)_2$, or a tertiary amine such as triethylamine may be added. The $CO_2$ removal additive may be employed in an amount within the range from about 1 to about 10 mole equivalent per mole of ester compound B, preferably from about 1 to about 4 mole equivalent per mole of ester compound B.

In one embodiment of the method of the invention, the enzymatic ammonolysis is carried out in the presence of ammonium carbamate employing a molar ratio of ammonium carbamate:compound B within the range from about 1:1 to about 5:1, preferably from about 2:1 to about 4:1, to supply ammonia gas in an amount within the range from about 1 to about 5 equivalents, preferably from about 2 to about 4 equivalents.

In a preferred embodiment, ammonia gas (from about 1 to about 5 equivalents, preferably from about 2 to about 4 equivalents) is employed alone or in conjunction with the ammonium carbamate.

In another preferred embodiment, the reaction of compound B and ammonia and/or ammonium carbamate is carried out in the presence of an aromatic solvent such as toluene. The reaction is run at a temperature from about 25° C. to about 80° C., preferably from about 40 to about 70° C.

The *Candida antarctica* lipase-B enzyme will be employed preferably in lyophilized form or in an immobilized form in catalytic amounts ranging from about 1% to about 50% w/v, preferably from about 5% to about 40% w/v.

In another aspect of the present invention, the intermediate A is used to produce intermediate J, as shown in the reaction set out below, by subjecting intermediate A to cyclopropanation via the Simmons-Smith reaction to produce compound H ([1S-(1α,3β,5α)]-3-(aminocarbonyl)-2-azabicyclo[3.1.0]hexane-2-carboxylic acid, 1,1-dimethylethyl ester) which is treated with HCl or methane sulfonic acid (MSA) to remove the BOC group and form the hydrochloride salt or MSA salt of the fragment (1S,3S,5S)-2-azabicyclo[3.1.0]-hexane-3-carboxamide J

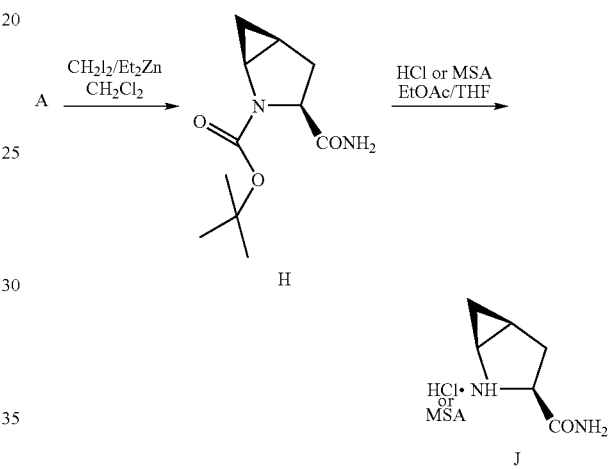

as described in detail in U.S. Provisional Application No. 60/431,814 filed Dec. 9, 2002 and as set out below.

The fragment (1S,3S,5S)-2-azabicyclo[3.1.0]hexane-3-carboxamide (Formula J) is used in the production of (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile and can be produced in accordance with the method depicted in the Scheme II set out hereafter.

The enzymatic ammonolysis process of the invention provides an efficient means for obtaining compounds of formula A, which are intermediates in the preparation of dipeptidyl pepidase IV inhibitors. Reduction or elimination of undesirable byproducts (which may be obtained employing prior art processes), preservation of enantiopurity (as opposed to chemical racemization) and shortening cycle times in an enviromentally friendly manner (waste reduction) may be achieved by employing the enzymatic ammonolysis method of the present invention. Another benefit derived from the enzymatic ammonolysis method of the invention is that the method may be conducted employing mild reaction conditions, namely temperatures vary from about 40° C. to about 70° C.

DETAILED DESCRIPTION OF THE INVENTION

Enzymatic ammonolysis of 4,5-dihydro-1H-pyrrole-1,5-dicarboxylic acid, 1-(1,1-dimethylethyl)-5-ethyl or methyl ester B to (5S)-5-aminocarbonyl-4,5-dihydro-1H-pyrrole-1-carboxylic acid, 1-(1,1-dimethylethyl) ester is depicted in Scheme I

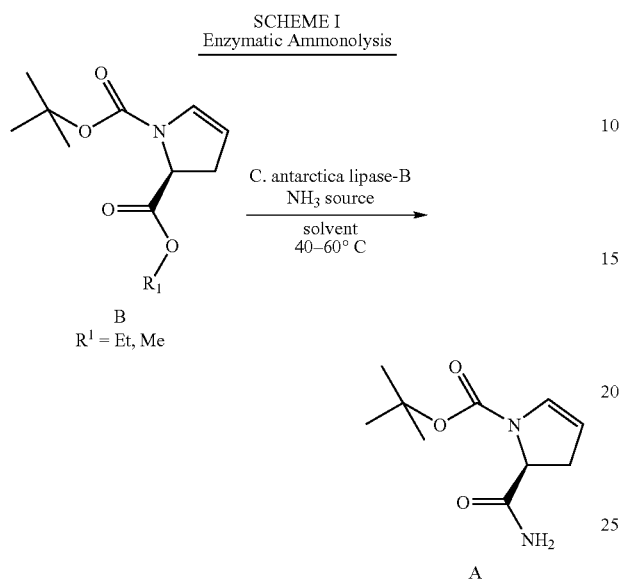

The starting compound B (R$_1$=Et) is prepared as described in U.S. Provisional Application No. 60/431,814, filed Dec. 9, 2002, and in Scheme II set out below.

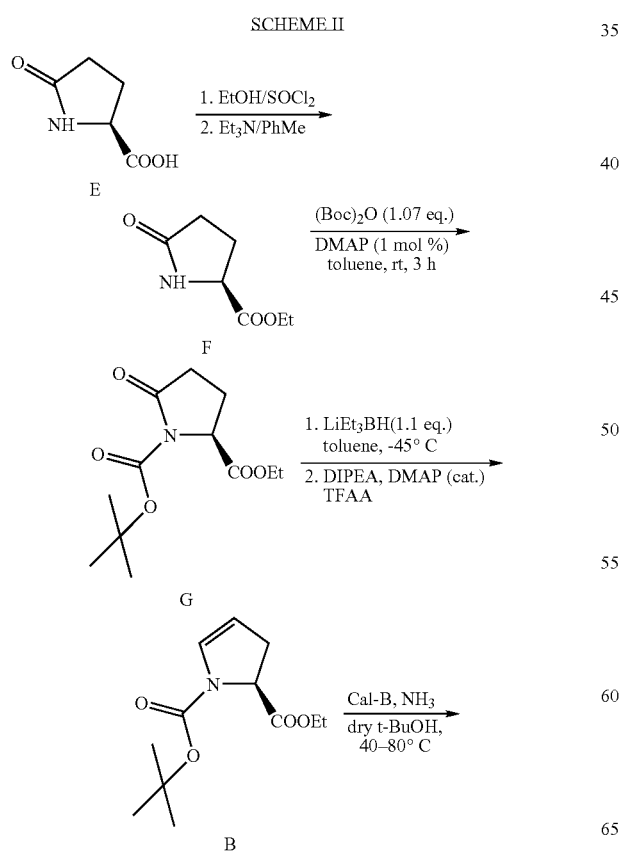

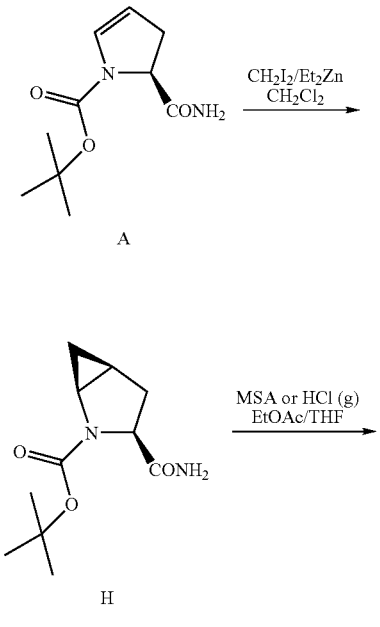

As shown in Scheme II, L-pyroglutamic acid (Formula E) is first esterified to produce the L-pyroglutamic acid ethyl ester (Formula F). This L-pyroglutamic acid ethyl ester is then BOC-protected on the nitrogen to produce (5S)-2-oxopyrrolidine-1,5-dicarboxylic acid, 1-(1,1-dimethylethyl),5-ethyl ester (Formula G). SuperHydride reduction and elimination is then performed to form 4,5-dihydro-1H-pyrrole-1,5-dicarboxylic acid, 1-(1,1-dimethylethyl),5-ethyl ester (Formula B, R$_1$=Et).

Compound B is then subjected to enzymatic ammonolysis, in accordance with the method of the invention to form compound A. (5S)-5-aminocarbonyl-4,5-dihydro-1H-pyrrole-1-carboxylic acid, 1-(1,1-dimethylethyl) ester (Formula A) is then cyclopropanated via the Simmons-Smith reaction to produce [1S-(1α,3β,5α)]-3-aminocarbonyl)-2-azabicyclo[3.1.0]hexane-2-carboxylic acid, 1,1-dimethylethyl ester (Formula H). BOC is then removed resulting in formation of an acid salt such as the hydrochloride salt or the methanesulfonic acid salt of the fragment (1S,3S,5S)-2-azabicyclo[3.1.0]hexane-3-carboxamide (Formula J).

The compound J is used to prepare the dipeptidyl peptidase IV inhibitor formula M compound in accordance with the following reaction Scheme III which is described in detail in U.S. Provisional Application No. 60/431,814 filed Dec. 9, 2002 and its corresponding non-provisional application Ser. No. 10/716,012 filed Nov. 18, 2003 which is incorporated herein by reference.

SCHEME III

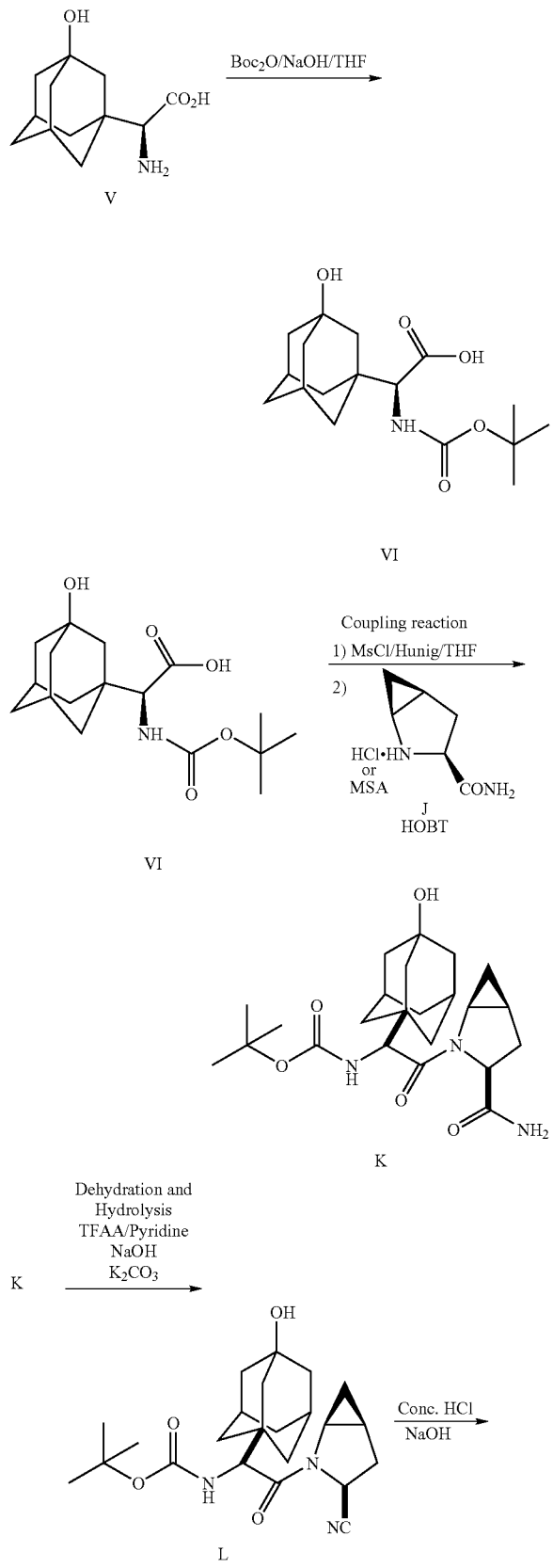

As shown in Scheme III, the fragment (αS)-α-amino-3-hydroxytricyclo[3.3.1.1³,⁷]decane-1-acetic acid (Formula V) is first BOC protected to produce (αS)-α[[(1,1-dimethylethoxy)carbonyl]amino]-3-hydroxytricyclo [3.3.1.1³,⁷]decane-1-acetic acid (Formula VI) by treating V with $BOC_{20}$ in the presence of base such as sodium hydroxide and separated via ethyl acetate (EtOAc) extraction to separate out free acid VI. Alternatively, in place of ethyl acetate, isopropyl acetate/heptane (2.25:1) may be employed to crystallize out free acid VI.

A solution of Formula VI compound in an appropriate organic solvent such as tetrahydrofuran (THF) (cooled to a temperature within the range from about 20 to about 30° C.) is treated with methanesulfonyl chloride (Mesyl Cl), and Hunig base (diisopropylethylamine or DIPEA) to form the corresponding methanesulfonic acid salt of VI.

A coupling reaction is then used to couple (αS)-α[[(1,1-dimethylethoxy)carbonyl]amino]-3-hydroxytricyclo [3.3.1.1³,⁷]decane-1-acetic acid, (Formula VI) to (1S,3S,5S)-2-azabicyclo[3.1.0]hexane-3-carboxamide (Formula J) methanesulfonic acid salt or HCl salt in the presence of 1-hydroxybenzotriazole (HOBT) or other known coupling agent to produce 3-(aminocarbonyl)-αS)-(α-(3-hydroxytricyclo[3.3.1.1³,⁷]dec-1-yl)-β-oxo-(1S,3S,5S)-2-azabicyclo [3.1.0]hexane-2-ethanecarbamic acid, 1,1-dimethylethyl ester (Formula K). Formula K compound is subjected to dehydration by treating compound K with organic base such as pyridine or triethylamine, and trifluoroacetic anhydride or other dehydrating agent such as phosphorus oxychloride ($POCl_3$) or cyanuric chloride, and then subjecting the reaction to hydrolysis by cooling to from about 25 to about 40° C. and treating with sodium hydroxide or other strong base such as KOH or LiOH to form Compound L. 3-cyano-(αS)-α-(3-hydroxytricyclo[3.3.1.1³,⁷]dec-1-yl)-β-oxo-(1S,3S, 5S)-2-azabicyclo[3.1.0]hexane-2-ethanecarbamic acid, 1,1-dimethylethyl ester (Formula L), which is then deprotected to form the dipeptidyl peptidase IV inhibitor (1S,3S,5S)-2-[(2S)-2-amino-2-(3-hydroxytricyclo[3.3.1.1³,⁷]dec-1-yl)-1-oxoethyl]-2-azabicyclo[3.1.0]hexane-3-carbonitrile (Formula M).

Compound L may be deprotected by treatment with strong acid such as hydrochloric acid as described with respect to Scheme IV.

SCHEME IV

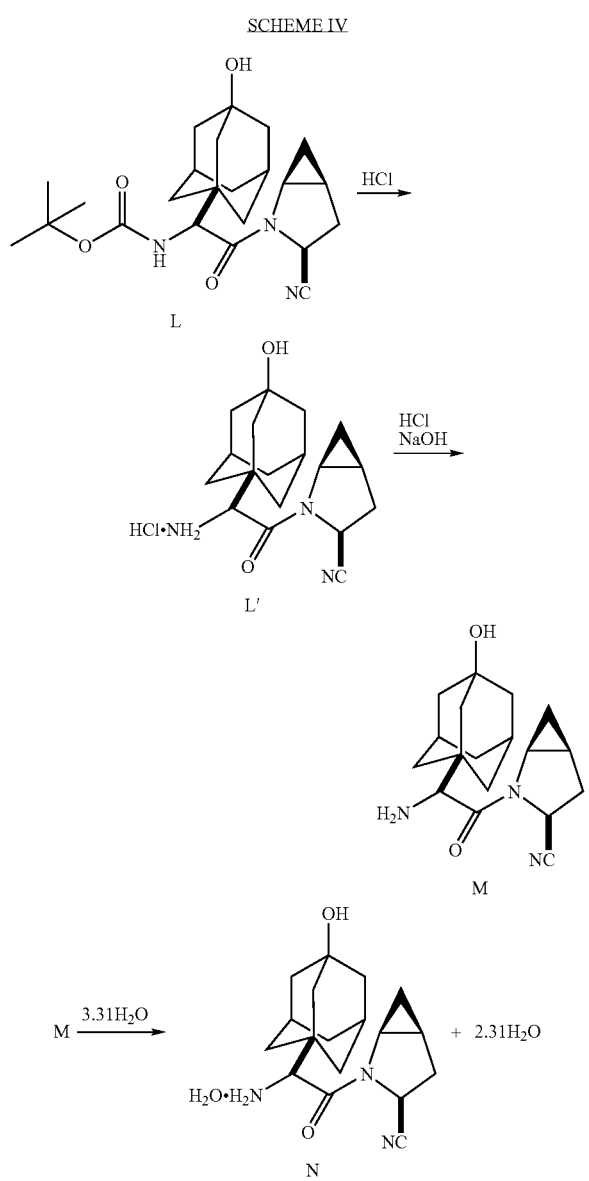

Referring to Scheme IV, the free base monohydrate M may be formed from the BOC-protected intermediate L as follows.

BOC-protected intermediate L is treated with concentrated hydrochloric acid in the presence of methylene chloride and methanol while maintaining reaction temperature within the range from about 20 and 25° C., to form hydrochloride salt L'. Hydrochloride salt L' is treated with hydrochloric acid and then sodium hydroxide or other strong base to form the free base M. Free base M is then treated with water to form the free base monohydrate N.

The fragment (1S,3S,5S)-2-azabicyclo[3.1.0]hexane-3-carboxamide (Formula J) may also be formed by removal of BOC from the intermediate [1S-(1α,3β,5α]-3-aminocarbonyl)-2-azabicyclo[3.1.0]hexane-2-carboxylic acid, 1,1-dimethylethyl ester (Formula H). In this embodiment, the method may further comprise a step for production of [1S-(1α,3β,5α]-3-aminocarbonyl)-2-azabicyclo[3.1.0]hexane-2-carboxylic acid, 1,1-dimethylethyl ester (Formula H) by cyclopropanation, preferably via a Simmons-Smith reaction of (5S)-5-aminocarbonyl-4,5-dihydro-1H-pyrrole-1-carboxylic acid, 1-(1,1-dimethylethyl) ester (Formula A).

The enzyme or microorganism employed in the method of the invention may be any enzyme or microorganism, regardless of origin or purity, having the ability to catalyze the conversion as described herein. Genera of microorganisms suitable as sources of catalyzing enzymes include *Candida*, *Bacillus*, *Pseudomonas* and *Aspergillus*.

The preferred enzyme for use in the method of the invention is *Candida antarctica* lipase-B (Cal-B) which is commercially available and sold under the name Chirazyme L-2 by Biocatalytics. In a preferred embodiment, the Cal-B enzyme will be immobilized on a support, preferably propylsiloxane-silica-PVA sol gel or other known supports such as Accurel MP-100 (available from Membrana GmbH) or Celite R-633 (diatomaceous earth) (available from Manville Co.) at a load within the range from about 40 to about 90% w/w, preferably from about 60 to about 80% w/w.

Enzymes and Microorganisms

With respect to the use of microorganisms, the method of the present invention may be carried out using any microbial cellular material having the ability to catalyze the conversion as described herein. The cells may be used in the form of intact wet cells or dried cells such as lyophilized, spray-dried or heat-dried cells. Cells may also be used in the form of treated cell material such as ruptured cells or cell extracts. The cells or cellular materials, such as isolated fungal mycelia, may be employed in the free-state or immobilized on a support such as by physical adsorption or entrapment. One or more species of microorganism may be employed when carrying out the instant process.

The method of the present invention may be carried out subsequent to the growth of the microorganism(s) employed, for example, by growing the microorganism(s) either in the presence or absence of a compound of the formula B starting material, harvesting and, preferably, washing (e.g., with water) the microbial materials, and then contacting the microbial materials obtained with the compound of the formula B starting material. The method of the present invention may also be carried out by in situ fermentation and reaction, that is, reaction in the presence of actively growing microorganisms.

Enzymes, when employed, are preferably derived from the aforementioned microorganisms, or they may be synthetically or otherwise prepared. For example, they may be derived from genetically engineered host cells. The use of the genetically engineered host cells themselves, or cells which have otherwise been modified, is also contemplated where such cells are capable of producing enzymes having the structure of enzymes derived from the above recited genera of microorganisms.

Reaction Conditions

The method of the present invention may be conducted in an organic medium in the absence of significant amounts of water. Examples of organic media suitable for this biotransformation include toluene, hexane, heptane, cyclohexane, methyl-tert-butyl ether, acetone, acetonitrile, dimethylsulfoxide, dimethylformamide, cyclohexane, xylene, trichlorotrifluoroethane, tetrahydrofuran, 1,4-dioxane, alkanols such as methyl or ethyl alcohol, branched tertiary alcohols like tert-butanol, tert-amyl alcohol, 3-methyl-3-pentanol and the like including mixtures of these.

Preferred solvents are toluene, 3-methyl-3-pentanol, and mixtures of methyl t-butyl ether:t-butanol from about 9:1 to 1:1. The reaction medium preferably contains between about 10 to about 100 mg of a compound of the formula B starting compound per ml of liquid medium.

The amount of enzyme added, where employed in the present process, is preferably an amount ranging from about 0.01 to about 1 g per g of the compound of formula B starting material.

The reaction medium is preferably held at a temperature between about 25° and 80° C. and is most preferably held between about 40° and about 70° C. Typical reaction times are between about 2.5 hours and about 72 hours. Reaction times may be reduced by increasing the reaction temperature and/or increasing the amount of enzyme added to the reaction solution. Molecular sieves 3A, 4A or 13X are prefereably employed to assist in ethanol removal.

EXAMPLES

The following Examples represent preferred embodiments of the present invention.

Example 1

Enzymatic Ammonolysis

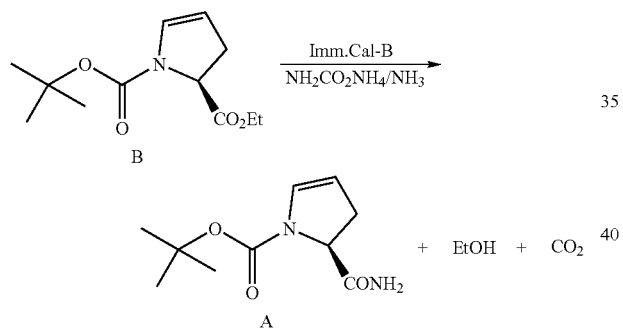

(2S)-2-Carbamoyl-2,3-dihydro-pyrrole-1-carboxylic acid tert-butyl ester (Compound A)

A reaction was conducted in a total volume of 10 ml using 50.0 g/l 4,5-dihydro-1H-pyrrole-1,5-dicarboxylic acid, 1-(1,1-dimethylethyl) 5-ethyl ester (Compound B) input (~75% purity), 25% w/v immobilized *Candida antarctica* lipase-B (Cal-B) (chirazyme L-2, c.-f., C2 lyo) and 1.7 equivalents of $NH_3$ (5 g/l ammonium carbamate and 50 ml of anhydrous ammonia gas). The reaction was run in a tightly sealed teflon flask at 75° C. with 200 rpm shaking in an incubator shaker. The yield of (5S)-5-aminocarbonyl-4,5-dihydro-1H-pyrrole-1-carboxylic acid, 1-(1,1-dimethylethyl)ester (Compound A) based on the starting material input was 93% after 42 hours.

Analytical:

The progress of the reaction was followed by HPLC analysis. Samples were diluted by adding 20 ul of reaction to 980 ul acetonitrile, and mixing.

| column: | YMC-Pack ODS-A, 150 mm × 6 mm |
|---|---|
| mobile phase: | C—$H_2O$ |
| | D - acetonitrile |
| flow rate: | 1.0 ml/min |
| gradient: | 0 min - 80% C/20% D |
| | 12 min - 25% C/75% D |
| | 12.01 min - 80% C/20% D |
| | 15.0 min - end |
| temperature: | 40° C. |
| UV detection: | 230 nm |
| injection: | 5 ul |
| retention times: | Compound B - 12.7 min |
| | Compound A - 6.7 min |

Example 2

Enzymatic Ammonolysis of 4,5-Dihydro-1H-pyrrole-1,5-dicarboxylic acid, 1-(1,1-dimethylethyl) 5-ethyl ester (Compound B)

Ammonolysis of 0.22 M (50 g/L) Compound B with solid ammonium carbamate (85 g/L, 5 mol equivalents) in toluene as solvent, and using lyophilized *Candida antarctica* Lipase-B (Cal-B) (16 g/L), at 50° C., 400 rpm, provided 60% and 84% yields of the corresponding amide (5S)-5-aminocarbonyl-4,5-dihydro-1H-pyrrole-1-carboxylic acid, 1-(1,1-dimethylethyl)ester (as determined by RP-HPLC) after reaction times of 18 h and 70 h, respectively.

Similar results were obtained with CAL-B immobilized on propylsiloxane-silica-PVA sol-gel (at a load of 8% w/w).

Reactions were carried out on a 0.2–0.4 mL scale using the crude ester process stream as the feed.

| Ester Feed: | 50 g/L (1/4 dilution of process stream comprising 200 g/L ester in PhMe) |
|---|---|
| $NH_3$ Donor Feed: | 85 g/L |
| Catalyst Feed: | 16 g/L |
| Reaction Temp: | 50° C. |
| Reaction Time: | 70 h |
| Product Yield (Anal): | 84% |
| Product Conc: | 46 g/L |
| Mass Productivity: | 2.9 g-Product/g-Catalyst |

Example 3

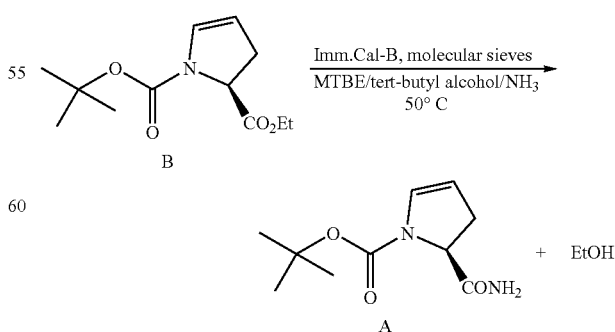

(2S)-2-Carbamoyl-2,3-dihydro-pyrrole-1-carboxylic acid tert-butyl ester (Compound A)

Immobilization of Cal-B Lipase onto Accurel MP-1000

Soluble *Candida antarctica* lipase, type B was obtained (Biocatalytics) with a specific activity of 505 IU/ml.

Soluble enzyme (750 mL, 0.38 MIU) was added to a mixture containing 1275 ml of water, 225 ml of isopropyl alcohol and 90 grams of Accurel MP-1000 (Membrana GmbH). The pH of the reaction mix was 5.2 without adjustment. The mixture was stirred with an overhead stirrer to evenly disperse the Accurel MP-1000 in the mixture for four hours at 25° C. The resin was filtered on a Buchner funnel fitted with Whatman #1 filter paper. The resin was washed with two volumes of water (4500 ml) and dried on the Buchner funnel with vacuum at room temperature until the resin weight was equal to the original input weight. The Accurel immobilized CAL-B enzyme was then stored at 4° C. The weight of the final product was 90 g with a specific activity of 1970 IU/gram, and a 47% yield (0.18 MIU).

The assay of the enzyme is as follows: 20 ml of emulsified reaction mixture containing 0.2M tributyrin, 2% gum arabicum, 0.2M $CaCl_2$, and 10 mM Hepes buffer, pH 7.5 is placed in a jacketed vessel at 25° C. Enzyme (soluble or immobilized) is added and the reaction titrated with 0.05N NaOH for five minutes on a Radiometer titrator (model PM290). The rate is measured between 2–4 min. If the rate is not linear in this range enzyme concentration is adjusted. Specific activity is reported as units per gram or ml and one unit is defined as the amount of enzyme that produces one micromole of butyric acid per minute (as measured by base uptake) under the above reaction conditions.

Preparation of Compound A

A solution of (5S)-4,5-dihydro-1H-pyrrole-1,5-dicarboxylic acid, 1-(1',1'-dimethylethyl) 5-ethyl ester (compound B) (54 mL, 0.1096 g/mL, quantified by $^1$H NMR using acetonitrile as internal standard; 24.5 mmol) in toluene was concentrated to remove solvent at 50° C. and 20 to 30 torr. The residue was dissolved in 200 mL t-butyl methylether (MTBE), and the solvent was removed again under the same conditions. The residue was then dissolved in 240 mL MTBE in a 3 neck round bottom flask equipped with a magnetic stir bar. To the MTBE solution, 60 mL 1.5M ammonium solution in t-BuOH (prepared by bubbling gaseous ammonium into t-BuOH) was added. The solution was stirred and was continuously pumped from the flask through a jacketed column of molecular sieve (Linde 4A, 60 g, pre-dried in a 250° C. oven overnight), and then through a jacketed column of Accurel-immobilized Cal-B (1970 IU/g, 15 g), and then back into the flask. The circulation speed was controlled at 15 mL/min. The column jacket temperature was controlled at 50° C. through a circulator, while the temperature of the solution in flask was controlled at 50° C. using a heating mantle. The progress of the reaction was monitored by HPLC (UV at 210 nm). Reaction reached 50% completion after 23 hr (based on HPLC area %). The reaction solution was then cooled to rt, and passed through a silica gel (Aldrich, cat# 23683-7, 150 g) column which was pre-equilibrated with ~300 mL solution of 4:1 MTBE/1.5M $NH_3$ in t-BuOH). The displaced solution from the column was discarded. 300 mL solution of 4:1 MTBE/1.5M $NH_3$ in t-BuOH was then passed into the column. The displaced solution (300 mL) contained 83% (Compound B) and 17% Compound A (HPLC area %), and was transferred to the 3-neck flask. The reaction was resumed under the same condition. The silica gel column was rinsed with 500 mL solution of 4:1 MTBE/1.5M $NH_3$ in t-BuOH. The collected solution contained primarily Compound A.

After another 20 hrs, reaction was found to be ~40% complete. After cooling to rt, the reaction solution was subjected to the silica gel column again in the same manner. The 300 mL fraction that contained mostly ester (94% Compound B, 6% Compound A) was transferred to the 3-neck flask. The reaction was resumed under the same condition. The silica gel column was rinsed with 500 mL solution of 4:1 MTBE/1.5M $NH_3$ in t-BuOH. The collected solution contained primarily Compound A.

After another 23 hrs, reaction was found to be ~40% complete. After cooling to rt, the reaction solution was subjected to the silica gel column again in the same way. The 300 mL fraction that contained mostly ester was concentrated and after further drying at high vacuum, a total of 2.35 g Compound B was recovered (92.1% area, 39.7% recovery yield). The silica gel column was rinsed with 500 mL solution of 4:1 MTBE/1.5M $NH_3$ in t-BuOH. Solution collected was combined with the two 500 mL fractions collected in previous two separations. After solvent removal and drying under high vacuum, a total of 3.41 g amorphous Compound A (98.7% area). Overall, the material balance from Compound B was 105% with a primary yield of 65.6% and 39.7% recovered ester.

The amorphous Compound A was then recrystallized. Thus, the 3.41 g amide was dissolved in 8 mL of ethyl acetate. Cyclohexane (24 mL) was added. After agitation for ~1 hr, product crystallized out. A total of 2.5 g of slightly yellowish solid was obtained (73.5% recovery, purity was 100 wt %, 100% area, 100% e.e). The product was identical by NMR to previously isolated and characterized Compound A. Drying of mother liquor yielded 0.9 g oil, which contained primarily Compound A (95% area).

Example 4

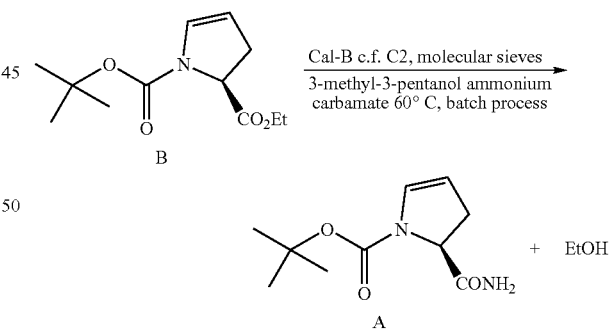

Immobilized Lipase and 3-Methyl-3-Pentanol as Solvent (Batch)

2.78 g of crude compound B in toluene (Ig of ester, 4.2 mmol) were dissolved in 20 mL of 3-methyl-3-pentanol. Immobilized CAL-B lipase c.f. C2 (1 g, Biocatalytics), 4A molecular sieves (2 g) and 1 g ammonium carbamate (12.8 mmol, ~3 eq.) were added to an Erlenmeyer flask and the mixture shaken at 60° C. and 200 rpm. After 66 h, reaction showed 99.2% mole conversion. The mixture is filtered through sintered glass, providing a sample where the starting ester could not be detected. Concentration by evaporation in vacuo provided 2.2 g of crude, AP=92%, potency 37% (representing 0.814 mg compound A (3.8 mmol, 93%). Filtration through silica of the sample using Hex:EtOAc (1:9) provided 995 mg of oil (AP=98.5%, potency=82%, representing 815 mg, 3.8 mmol, 93%). Crystallization by dissolving the residue in 1.5 mL EtOAc and adding ~7 mL cyclohexane provided white crystals, collected and dried (555 mg, 62%) AP=99.4%, potency 92% (w/w by HPLC).

Example 5

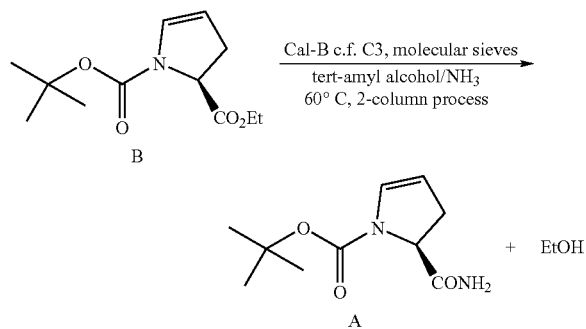

Immobilized Lipase and Tert-Amyl Alcohol as Solvent (2-Column Process)

14 mL of crude toluene solution of compound B (36% potency, 5 g of activity) where mixed with 86 mL of a saturated solution of NH₃ in tert-amyl alcohol. This mixture was placed in a 3-neck RBF fitted with a condenser and heated at 60° C. The solution is stirred with a magnetic bar and passed through two columns (both kept at 60° C.), one containing 2.5 g immobilized lipase C3 (7142 U/g) and another containing 5 g of 4A molecular sieves previously dried in the oven at >100° C. Flow rate is 10–15 mL/min. Conversion at 24 h is 78%, at 46 h is 92%. The resulting solution was filtered, and the filtrate was concentrated under vacuum, then loaded with hexane:ethyl acetate (4:1) onto a silica column (~10 g) and eluted using hexane, hex:EtOAc 80:20, hex:EtOAc 65:35, hex:EtOAc 35:65, hex:EtOAc 1:1. Fractions from the last two eluents contained Compound A and were pooled, concentrated and crystallized using EtOAc as solvent and ~7 volumes hexanes as antisolvent. White crystals were collected and dried (2.9 g, 65%) AP=99.6%, potency 97% (w/w by HPLC).

Example 6

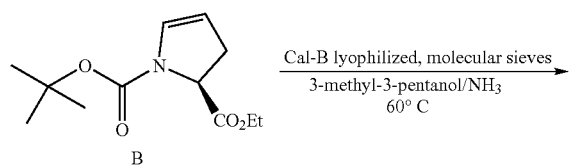

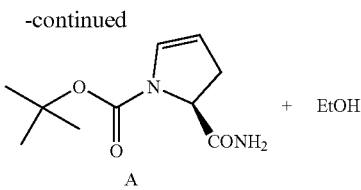

Lyophilized Powder, 3-methyl-3-pentanol as Solvent, Batch Process 5 g of compound B ethyl ester previously purified by extraction into heptane from MeCN were dissolved in 100 mL of 3-methyl-3-pentanol saturated with ammonia. 10 g of dried 4A molecular sieves were added followed by 0.5 g of CAL-B lipase lyophilized powder. The reaction was shaken in an Erlenmeyer flask at 60° C.; within 66 h the molar conversion was >97% (HPLC). The enzyme and sieves were filtered off, and the filtrate was concentrated and filtered through SiO₂ (~10 g), loading as a hexanes:EtOAc (4:1) solution. This was eluted with hexanes, hex:EtOAc 80:20, hex:EtOAc 35:65, hex:EtOAc 1:1. Fractions from the last two eluents contained Compound A and were pooled, concentrated and crystallized using EtOAc as solvent and ~7 volumes hexanes as antisolvent. White crystals were collected and dried (2.8 g, 64%) AP=99.9%, potency 99% (w/w by HPLC).

Example 7

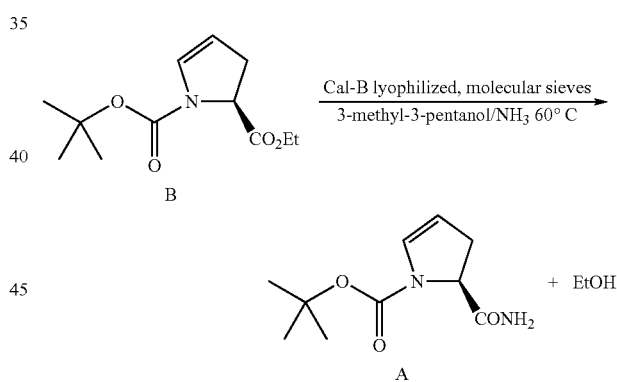

Lyophilized Powder, 3-methyl-3-pentanol as Solvent, Batch Process 5 g of compound B ethyl ester previously purified by extraction into heptane from toluene were dissolved in 95 mL of 3-methyl-3-pentanol saturated with ammonia. 10 g of dried 4A molecular sieves were added followed by 2.5 g of CAL-B lipase lyophilized powder. Reaction was magnetically stirred in a round bottom flask at 60° C.; within 18 h the molar conversion was >95% (HPLC). Enzyme and sieves were filtered off, and the filtrate was concentrated, diluted with hexanes:EtOAc (4:1) and pad-filtered through SiO₂ (~20 g) using hex:EtOAc 80:20 to remove residual ester, and then hex:EtOAc 20:80 to collect product A. Rich filtrate was concentrated and crystallized at room temperature using EtOAc as solvent and ~7 volumes cyclohexane as

Example 8

Enzymatic Ammonolysis of 4,5-Dihydro-1H-pyrrole-1,5-dicarboxylic acid 1-(1',1'-dimethylethyl)-5-ethyl ester by *Candida antarctica* Lipase B Immobilized on Celite R-633

Preparation of *Candida antarctica* Lipase B-Celite R-633 Biocatalyst

A solution of 3-aminopropyltrimethoxysilane (1.32 mL, obtained from Aldrich, WI, USA) in methanol (4 mL) was added to a mixture of poly(ethylene glycol) diglycidyl ether (2 g, purchased from Aldrich, Wis., USA) and zirconium (IV) chloride (50 mg, obtained from Aldrich, Wis., USA) stirred under nitrogen at 400 rpm, 40° C. After 1 h, the temperature was raised to 80° C. and stirring continued for 20 h. The mixture was then diluted 1/3 into absolute ethanol and a portion of the resulting solution (1 mL) was coated onto Celite R-633 (1 g, 0.5-2 mm granules, obtained from Manville Co, USA) and the wet granules dried in a fluidized bed dryer at RT for 0.5 h. The dry powder was then baked in an oven, in air at 120° C. for 20 h, to give ca. 1.17 g of modified Celite-R633. *C. antarctica* lipase B powder (0.20 g, 125 kU g$^{-1}$, obtained from Biocatalytics, Inc., CA, USA) was dissolved in ice-cold phosphate buffer (0.8 mL, 0.2 M, pH 7.0), the solution mixed with poly(ethylene glycol) stock (0.4 mL, 25% w/w of PEG-100, obtained from Sigma, WI, USA, dissolved in 0.2 M phosphate buffer, pH 7.0), and the mixture coated onto the modified Celite R-633 (1 g). The coated material was dried under vacuum over Drierite at RT, 20 h, to yield 1.32 g of immobilizate, with an enzyme loading of ca. 15% w/w.

Ammonolysis with Immobilized *Candida antarctica* Lipase B-Celite R-633 Biocatalyst A 20 mL vial was charged with the immobilized biocatalyst (0.2 g), ammonium carbamate (0.2 g), calcium chloride beads (0.2 g), and a solution of 4,5-dihydro-1H-pyrrole-1,5-dicarboxylic acid 1-(1',1'-dimethylethyl)-5-ethyl ester (4.0 mL, ca. 12% w/w solution in toluene, equivalent to 0.48 g of ester). The vial was sealed with a double PTFE-silicone-PTFE septum cap equipped with a suspended magnetic stirrer and the reaction mixture stirred at 350–400 rpm, 50° C. After 8 h, the vial was opened and charged with additional ammonium carbamate (0.1 g) and calcium chloride (0.2 g), the vial resealed, and the reaction continued for another 42 h, at which time HPLC analysis indicated that ca. 82% conversion of the ester to the amide had been reached.

Analytical

Samples were analyzed by RP-HPLC on a Shimadzu LC-10 system: Phenomenex Synergi Max-RP, 4 um, 2×50 mm column, gradient eluted with 10 to 100% B over 8 min, where A=8:2 (v/v) water-methanol with 0.05% TFA and B=8:2 (v/v) acetonitrile-methanol with 0.05% TFA. Flow rate at 0.6 mL min$^{-1}$, injection at 5 uL, temperature at RT, and detection at 220 and 225 nm. RT(Ester)=6.9 min and RT(amide)=2.0 min.

Example 9

Enzymatic ammonolysis of 4,5-Dihydro-1H-pyrrole-1,5-dicarboxylic acid 1-(1',1'-dimethylethyl)-5-ethyl ester by *Candida antarctica* Lipase B

*C. antarctica* lipase B powder (0.12 g, 125 kU g$^{-1}$, obtained from Biocatalytics, Inc., Calif., USA), a solution of 4,5-dihydro-1H-pyrrole-1,5-dicarboxylic acid 1-(1',1'-dimethylethyl)-5-ethyl ester (6.0 mL as a 20% w/w solution in toluene, equivalent to 1.2 g or 5.9 mmol of ester), ammonium carbamate (0.4 g, 5.1 mmol), calcium chloride (0.6 g), sodium hydroxide-coated silica (Ascarite-Aldrich) (0.6 g, placed in a perforated polypropylene tube suspended in the vial headspace) and a stirbar were charged into a 20 mL vial. The vial was sealed with a septum cap, and the reaction mixture stirred at 400 rpm, at 50° C. for 72 h. After 72 h, HPLC analysis indicated that 94% conversion of substrate had been achieved, with 87% conversion to the amide, corresponding to a productivity of 7.7 g of amide per g of enzyme powder.

Analytical

Samples were analyzed by RP-HPLC on a Shimadzu LC-10 system: Phenomenex Synergi Max-RP, 4 um, 2×50 mm column, gradient eluted with 10 to 100% B over 8 min, where A=8:2 (v/v) water-methanol with 0.05% TFA and B=8:2 (v/v) acetonitrile-methanol with 0.05% TFA. Flow rate at 0.6 mL min$^{-1}$, injection at 5 uL, temperature at RT, and detection at 220 and 225 nm. RT(Ester)=6.9 min and RT(amide)=2.0 min.

Example 10

Enzymatic ammonolysis of 4,5-Dihydro-1H-pyrrole-1,5-dicarboxylic acid 1-(1',1'-dimethylethyl)-5-ethyl ester by Immobilized *Candida antarctica* Lipase B Preparation of *Candida antarctica* Lipase B-Silicone Biocatalyst

*C. antarctica* lipase B powder (0.15 g, 125 kU g$^{-1}$, obtained from Biocatalytics, Inc., CA, USA) was thoroughly blended with fumed silica powder (0.15 g, Aerosil, purchased from Aldrich, WI, USA), and this mixed with silanol-terminated poly(dimethylsiloxane) (0.45 mL, comprising a 1:1:1 (v/v) blend of 90, 750 and 1,800 kCst oligomers, obtained from Aldrich, Wis., USA) to form a thick paste. This was then rapidly blended with a mixture of poly(diethyl silicate, obtained from Geleste, PA, USA) (0.18 mL) and tin(II) octoate (12 uL, obtained from Aldrich, WIS., USA), and the resulting paste coated onto the inside sidewall of a 20 mL glass reaction vial and allowed to cure at room temperature for 18 h. This yielded 0.73 g of immobilizate, with an enzyme powder loading of 21% w/w.

Ammonolysis with Immobilized *Candida antarctica* Lipase B-Silicone Biocatalyst

The vial containing immobilized biocatalyst was charged with a solution of 4,5-dihydro-1H-pyrrole-1,5-dicarboxylic acid 1-(1',1'-dimethylethyl)-5-ethyl ester (6.0 mL as a 20% w/w solution in toluene, equivalent to 0.75 g or 3.11 mmol of ester), ammonium carbamate (280 mg, 3.6 mmol), calcium chloride (0.3 g), Ascarite (3 g, placed in a perforated polypropylene tube suspended in the vial headspace) and a stirbar. The vial was sealed with a septum cap and the reaction mixture stirred at 400 rpm, 50° C. After 48 h, HPLC analysis indicated that complete conversion of substrate had been achieved, and the vial was drained of reaction mixture, the immobilized catalyst was washed with toluene (2×5 mL, stirred at 400 rpm, RT, 15 min), and the vial recharged with reaction mixture and Ascarite, and the experiment repeated as above. Four 48 h batch ammonolysis reactions implemented as above provided the following results: The initial rates of amide formation (measured at 2 h after commencement of reaction) were 1.4, 1.4, 1.2 and 1.0 mol h$^{-1}$ kg$^{-1}$, and the amide yields (at 48 h) were 87, 88, 85 and 82% (by HPLC), respectively. No significant racemization of the amide product was detected by chiral HPLC. The average amide yield was 85%, and the cumulative amide production estimated (by HPLC) at 2.26 g, corresponding to a net productivity of 15.1 g of amide per g of enzyme powder. From these results it was apparent that the immobilized biocatalyst could be reused at least 10 times, with an attainable productivity of at least 30 g of amide per g of enzyme powder.

Analytical

Samples were analysed by RP-HPLC on a Shimadzu LC-10 system: Phenomenex Synergi Max-RP, 4 um, 2×50 mm column, gradient eluted with 10 to 100% B' over 8 min, where A'=8:2 (v/v) water-methanol with 0.05% TFA and B'=8:2 (v/v) acetonitrile-methanol with 0.05% TFA. Flow rate at 0.6 mL min$^{-1}$, injection at 5 uL, temperature at RT, and detection at 220 and 225 nm. RT(Ester)=6.9 min and RT(amide)=2.0 min.

What is claimed is:

1. A method for the preparation of a compound of the formula

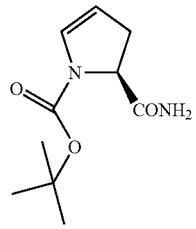

A which comprises the step of contacting a compound of the formula B

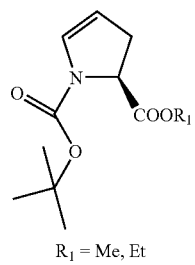

B $R_1$ = Me, Et with an enzyme which is fraction B lipase from the yeast *Candida antarctica*, which is capable of catalyzing the ammonolysis of said compound of the formula B, to yield said compound of formula A, in the presence of a source of ammonia, and effecting said ammonolysis to form the formula A compound.

2. The method as defined in claim 1 wherein said *Candida antarctica* lipase-B is immobilized.

3. The method as defined in claim 1 wherein said *Candida antarctica* lipase-B is immobilized on a support which is propylsiloxane-silica-PVA sol-gel or Accurel MP-1000, or Celite R-633.

4. The method as defined in claim 1 wherein said *Candida antarctica* lipase-B is lyophilized.

5. The method as defined in claim 1 wherein the ammonolysis is carried out at a temperature within the range from about 25° C. to about 80° C.

6. The method as defined in claim 1 wherein said ammonolysis is carried out in the presence of ammonium carbamate and/or ammonia.

7. The method as defined in claim 1 wherein said ammonolysis is carried out in the presence of 4A molecular sieves and/or anhydrous $CaCl_2$.

8. The method as defined in claim 1 wherein said ammonolysis is carried out in the presence of ammonia or ammonium carbamate and 4A molecular sieves employing toluene or 3-methyl-3-pentanol as the solvent.

9. The method as defined in claim 1 wherein said ammonolysis is carried out in the presence of ammonia or ammonium carbamate and 4A molecular sieves employing a branched tertiary alcohol as the solvent.

10. The method as defined in claim 1 wherein said ammonolysis is carried out by an immobilized biocatalyst enclosed in a column reactor with 4A molecular sieves and/or anhydrous $CaCl_2$ enclosed in another column following said column reactor.

11. The method as defined in claim 1 which includes the steps of contacting the compound of formula B with *Candida antarctica* lipase-B in the presence of an ammonia source maintaining a reaction temperature within the range from about 25° C. to about 80° C. and a reaction time from about 2.5 to about 72 hours.

12. The method as defined in claim 11 wherein the compound of formula B is contacted with *Candida antarctica* lipase B in the presence of ammonium carbamate and/or anhydrous ammonia gas.

13. The method as defined in claim 9 wherein the compound of formula B is contacted with *Candida antarctica* lipase B in the presence of ammonium carbamate and/or anhydrous ammonia gas in t-butanol, t-amyl alcohol, or a mixture of methyl t-butyl ether:t-butyl alcohol (about 4:1) as a solvent.

14. The method as defined in claim 8 wherein the compound of formula B is contacted with *Candida antarctica* lipase B immobilized on a support which is propylsiloxane-silica-PVA sol-gel or Accurel MP-1000, or Celite R-633.

* * * * *